US012611408B2

(12) United States Patent
Brichta

(10) Patent No.: US 12,611,408 B2
(45) Date of Patent: Apr. 28, 2026

(54) METHODS FOR TREATING NAIL BRITTLENESS, FRAGILITY, OR PITTING

(71) Applicant: Chemistry RX, Folcroft, PA (US)

(72) Inventor: Lars Brichta, Brooklyn, NY (US)

(73) Assignee: Chemistry RX, Folcroft, PA (US)

( * ) Notice: Subject to any disclaimer, the term of this patent is extended or adjusted under 35 U.S.C. 154(b) by 470 days.

(21) Appl. No.: 17/250,123

(22) PCT Filed: Jun. 4, 2019

(86) PCT No.: PCT/US2019/035415
§ 371 (c)(1),
(2) Date: Dec. 1, 2020

(87) PCT Pub. No.: WO2019/236596
PCT Pub. Date: Dec. 12, 2019

(65) Prior Publication Data
US 2021/0213021 A1      Jul. 15, 2021

Related U.S. Application Data

(60) Provisional application No. 62/680,054, filed on Jun. 4, 2018.

(51) Int. Cl.
| | |
|---|---|
| A61K 31/519 | (2006.01) |
| A61K 9/127 | (2025.01) |
| A61K 31/122 | (2006.01) |
| A61K 31/497 | (2006.01) |
| A61K 31/4985 | (2006.01) |
| A61K 31/506 | (2006.01) |
| A61K 31/529 | (2006.01) |
| A61K 31/5377 | (2006.01) |
| A61K 31/541 | (2006.01) |
| A61K 31/5575 | (2006.01) |
| A61K 31/58 | (2006.01) |
| A61K 31/585 | (2006.01) |
| A61K 31/655 | (2006.01) |
| A61K 31/7076 | (2006.01) |
| A61K 35/62 | (2006.01) |
| A61K 47/20 | (2006.01) |
| A61P 17/00 | (2006.01) |
| A61P 17/14 | (2006.01) |
| A61Q 3/00 | (2006.01) |

(52) U.S. Cl.
CPC ............ *A61K 31/519* (2013.01); *A61K 9/127* (2013.01); *A61K 31/122* (2013.01); *A61K 31/497* (2013.01); *A61K 31/4985* (2013.01); *A61K 31/506* (2013.01); *A61K 31/529* (2013.01); *A61K 31/5377* (2013.01); *A61K 31/541* (2013.01); *A61K 31/5575* (2013.01); *A61K 31/58* (2013.01); *A61K 31/585* (2013.01); *A61K 31/655* (2013.01); *A61K 31/7076* (2013.01); *A61K 35/62* (2013.01); *A61K 47/20* (2013.01); *A61P 17/00* (2018.01); *A61P 17/14* (2018.01)

(58) Field of Classification Search
None
See application file for complete search history.

(56) References Cited

U.S. PATENT DOCUMENTS

| | | |
|---|---|---|
| 2008/0280838 A1 | 11/2008 | Cho et al. |
| 2011/0130706 A1 | 6/2011 | Kellogg et al. |
| 2011/0130711 A1 | 6/2011 | Lederman et al. |
| 2011/0130748 A1 | 6/2011 | Kellogg et al. |
| 2011/0212167 A1 | 9/2011 | Ali |
| 2012/0259311 A1 | 10/2012 | Hirshberg |
| 2014/0065153 A1* | 3/2014 | Christiano ............... A61Q 7/00 424/139.1 |
| 2014/0276359 A1 | 9/2014 | Alvarez |
| 2015/0284405 A1 | 10/2015 | Trzupek et al. |
| 2017/0095621 A1 | 4/2017 | Hirshberg |
| 2017/0174772 A1* | 6/2017 | Nirula ..................... A61P 17/06 |
| 2017/0224760 A1 | 8/2017 | Garruto et al. |
| 2018/0193320 A1 | 7/2018 | Kaupinen |
| 2018/0289772 A1 | 10/2018 | Song |
| 2019/0231782 A1* | 8/2019 | Chen ....................... A61P 37/02 |
| 2020/0038338 A1 | 2/2020 | Wambier et al. |
| 2020/0101000 A1 | 4/2020 | Cotsarelis et al. |
| 2021/0353600 A1 | 11/2021 | Brichta |
| 2021/0353622 A1 | 11/2021 | Brichta |

FOREIGN PATENT DOCUMENTS

| | | |
|---|---|---|
| BR | 102018069553 | 4/2020 |
| EP | 3695832 | 8/2020 |
| WO | 1991/007431 | 5/1991 |
| WO | 1994/027594 | 12/1994 |

(Continued)

OTHER PUBLICATIONS

Lee, Ji Su, et al. "Nail involvement in patients with moderate-to-severe alopecia areata treated with oral tofacitinib." Journal of Dermatological Treatment 29.8 (2018): 819-822. (Year: 2018).*

(Continued)

*Primary Examiner* — Bethany P Barham
*Assistant Examiner* — Peter Anthopolos
(74) *Attorney, Agent, or Firm* — FisherBroyles, LLP; Christy G. Rothwell

(57) ABSTRACT

Compositions and methods for treating hair loss and/or nail brittleness, fragility, and pitting, particularly in pediatric patients, using topically administered JAK/STAT inhibitors and one or more penetration enhancer are described herein.

7 Claims, No Drawings

(56) References Cited

FOREIGN PATENT DOCUMENTS

| WO | WO 2010/036947 | | 4/2010 |
|----|----------------|----|--------|
| WO | WO 2011/082235 | | 7/2011 |
| WO | WO 2012/061537 | | 5/2012 |
| WO | WO 2012/106249 | | 8/2012 |
| WO | WO 2013/149194 | | 10/2013 |
| WO | WO 2016/179605 | | 11/2016 |
| WO | 2018/042352 | A1 | 3/2018 |
| WO | WO 2019/138291 | | 7/2019 |
| WO | WO 2019/152232 | | 8/2019 |
| WO | WO 2019/232242 | | 12/2019 |
| WO | WO 2019/236596 | | 12/2019 |
| WO | WO 2020/046820 | | 3/2020 |
| WO | WO 2020/136650 | | 7/2020 |
| WO | WO 2021/240163 | | 12/2021 |

OTHER PUBLICATIONS

Cheng, Michelle W., et al. "Successful Treatment of Severe Alopecia Areata With Oral or Topical Tofacitinib." Journal of drugs in dermatology: JDD 17.7 (2018): 800-803. (Year: 2018).*

Dhayalan, Arjun, and Brett A. King. "Tofacitinib citrate for the treatment of nail dystrophy associated with alopecia universalis." JAMA dermatology 152.4 (2016): 492-493. (Year: 2016).*

U.S. Appl. No. 17/302,781, filed May 12, 2021.

European Extended Search Report for European No. 19815877.6 dated Jul. 14, 2022, 15 pages.

International Search Report and Written Opinion dated Aug. 26, 2021 for International Application No. PCT/US2021/070540, 9 pages.

International Search Report and Written Opinion dated Aug. 26, 2021 for International Application No. PCT/US2021/070539, 7 pages.

International Search Report and Written Opinion dated Sep. 16, 2019 for International Application No. PCT/US2019/035415, 13 pages.

Indian Hearing Objections dated Oct. 20, 2022 for Indian Patent Application No. 202027057073, 9 pages.

Bay Art, Cheryl B. et al., "Topical Janus Kinase Inhibitors for the Treatment of Pediatric Alopecia Areata", Journal of the American Academy of Dermatology, 2017, 77.1: 167-170, dated Dec. 31, 2017.

Contin et al., "Male Androgenetic Alopecia Treated with Microneedling Alone or Associated with Injectable Minoxidil by Microinfusion of Drugs into the Skin." Jun. 3, 2016, 4 pages.

Dha Y Alan, Aijun et al, "Tofacitinib Citrate for the Treatment of Nail Dystrophy Associated with Alopecia Universalis", JAMA Dermatology, 2016, 152.4: 492-493, dated Dec. 31, 2016.

Dhurat et al., "A Randomized Evaluator Blinded Study of Effect of Microneedling in Androgentic Alopeica: A Piot Study." Jan.-Mar. 2013, 10 pages.

Gentile et al., "Regenerative Biotechnologies in Plastic Surgery: A Multicentric, Retrospective, Case-Series Study on the Use of Micro-Needling with Low-Level Light/Laser Therapy as a Hair Growth Boost in Patients Affected by Androgenetic Alopecia", Nov. 3, 2021, 5 pages.

Kim et al., The Skin-Permeation-Enhancing Effect of Phosphatidylcholine: Caffeine as a Model Active Ingredient. Journal of Cosmetic Science. 53. 363-74. (Year: 2002).

Sengupta et al. (2016). Improved Skin Penetration. AAPA PharmSciTech, vol. 17, No. 2, Apr. 2016. (Year: 2016).

"MilliporeSigma. Poloxamer 188 Solution", Web page, <https://www.sigmaaldrich.com/US/en/product/sigma/p5556?gclid=Cj0KCQjw8uOWBhDXARlsAOxKJ2HXo8yt61Awput19pfVX9T7GZGSxT8VS28oysxTV9DmPrCgxtHkDlaAkJ3EALw_wcB (Year: 2022)>, 5 pages, accessed on Aug. 31, 2022.

"Topical Tacrolimus", Web page <https://www.medicaljournals.se/acta/download/10.1080/000155502320624203/>, "Topical Tacrolimus (FK506): Treatment Failure in Four Cases of Alopecia Universalis", 2 pages, accessed on Aug. 31, 2022.

"Treatment of Alopecia", Web page <https://www.applications.emro.who.int/imemrf/J_Pak_Assoc_Dermatol/J_Pak_Assoc_Dermatol_2015_25_3_197_201.pdf>, "Efficacy of Topical Tacrolimus 0.1% and Clobetasol Propionate 0.05% in the Treatment of Alopecia Areata", 5 pages, access on Aug. 31, 2022.

Office Action issued in Japanese Patent Application No. 2020-568468, Jun. 20, 2023, pp. 5.

Chetyl et al., Topical Janus kinase inhibitors for the treatment of pediatric alopecia areata, Journal of the American Academy of Dermatology, Jul. 2017, vol. 77, No. 1, pp. 167-170. https://doi.org/10.1016/j.jaad.2017.03.024.

* cited by examiner

METHODS FOR TREATING NAIL BRITTLENESS, FRAGILITY, OR PITTING

CROSS-REFERENCE TO RELATED APPLICATIONS

This application is filed under 35 U.S.C. § 371 as the U.S. national phase of International Patent Application No. PCT/US19/35415, filed Jun. 4, 2019, which designated the United States and which claims the benefit of U.S. Provisional No. 62/680,054, entitled "Topical Compositions for Stimulating Hair Growth," filed Jun. 4, 2018, the entirety of which is hereby incorporated by reference.

GOVERNMENT INTERESTS

Not applicable

PARTIES TO A JOINT RESEARCH AGREEMENT

Not applicable

INCORPORATION OF MATERIAL ON COMPACT DISC

Not applicable

BACKGROUND

Not applicable

SUMMARY OF THE INVENTION

Various embodiments are directed to methods for treating hair loss including the step of topically administering to a subject in need of treatment a composition containing up to about 15% (w/w) JAK/STAT inhibitor and a penetration enhancer. In some embodiments, the subject may be a pediatric subject, and in particular embodiments, the subject may be about 1 year to about 15 years of age. In certain embodiments, the subject may have a disorder such as, for example, alopecia areata, alopecia totalis, alopecia universalis, vitiligo, graft versus host disease, telogen effluvium, tinea capitis (dermatophytosis), hypotrichosis, hereditary hypotrichosis simplex, frontal fibrosing alopecia, cicatricial alopecia, lichen planopilaris, ring alopecia, and chemotherapy induced alopecia.

In various embodiments, the one or more penetration enhancer may include carriers and vehicles, chemical penetration enhancers, diols, polyols, fatty acids, fatty alcohols, fatty acid esters, surfactants, pyrrolidones, and combinations thereof. In some embodiments, the penetration enhancer may be a chemical penetration enhancer such as, for example, dimethyl sulphoxide (DMSO), decylmethyl sulfoxide, azone (1-dodecylazacycloheptan-2-one or laurocapran), pyrrolidones, oxazolidinones, urea, and combinations thereof. The penetration enhancer, in such embodiments, may be about 1% (w/w) to about 20% (w/w) of the total composition.

In some embodiments, the JAK/STAT inhibitor may be, for example, ruxolitinib (INCB 018424), tofacitinib (CP690550), AG490, momelotinib (CYT387), partcitinib (SB 1518), baricitinib (LY3009104), fedratinib (TG101348), BMS-911543, lestaurtinib (CEP-701), fludarabine, epigallocatechin-3-gallate (EGCG), baricitinib, momelotinib, pacritinib, peficitinib, ABT 494, AT 9283, decernmotinib, filgotinib, gandotinib, INCB 39110, PF 4965842, R348, AZD 1480, BMS 911543, cerdulatinib, INCB 052793, NS 018, C 410, CT 1578, JTE 052, PF 6263276, R 548, TG 02, *Lumbricus rebellus* extract, ARN 4079, AR 13154, UR 67767, CS510, VR588, DNX 04042, hyperforin, and pharmaceutically acceptable salts and combinations thereof. Such compositions may include about 0.5% (w/w) to about 10% (w/w) JAK/STAT inhibitor based on the total composition.

In some embodiments, the composition may include a base, and in particular embodiments, the base may be a liposomal base. The base in such embodiments may make up about 65% (w/w) to about 90% (w/w) of the total composition. In some embodiments, the compositions may further include a secondary active agent such as, for example, minoxidil, bimatoprost, latanoprost, finasteride, spironolactone, aldactone, kenalog-10, kenalog-40, aristospan, triamcinolone, azulfidine, sulfasalazine, sulfazine, and combinations thereof. The secondary active agent may make up about 0.25% (w/w) to about 15% (w/w) of the total composition.

Other embodiments are directed to methods for treating nail brittleness, fragility, or pitting by topically administering to a subject in need of treatment a composition containing up to about 15% (w/w) JAK/STAT inhibitor and a penetration enhancer. In some embodiments, the subject may be a pediatric subject, and in particular embodiments, the subject may be about 1 year to about 15 years of age. In certain embodiments, the subject may have a disorder such as, for example, alopecia areata, alopecia totalis, alopecia universalis, vitiligo, graft versus host disease, telogen effluvium, tinea capitis (dermatophytosis), hypotrichosis, hereditary hypotrichosis simplex, frontal fibrosing alopecia, cicatricial alopecia, lichen planopilaris, ring alopecia, and chemotherapy induced alopecia.

In various embodiments, the one or more penetration enhancer may include carriers and vehicles, chemical penetration enhancers, diols, polyols, fatty acids, fatty alcohols, fatty acid esters, surfactants, pyrrolidones, and combinations thereof. In some embodiments, the penetration enhancer may be a chemical penetration enhancer such as, for example, dimethyl sulphoxide (DMSO), decylmethyl sulfoxide, azone (1-dodecylazacycloheptan-2-one or laurocapran), pyrrolidones, oxazolidinones, urea, and combinations thereof. The penetration enhancer, in such embodiments, may be about 1% (w/w) to about 20% (w/w) of the total composition.

In some embodiments, the JAK/STAT inhibitor may be, for example, ruxolitinib (INCB 018424), tofacitinib (CP690550), AG490, momelotinib (CYT387), partcitinib (SB 1518), baricitinib (LY3009104), fedratinib (TG101348), BMS-911543, lestaurtinib (CEP-701), fludarabine, epigallocatechin-3-gallate (EGCG), baricitinib, momelotinib, pacritinib, peficitinib, ABT 494, AT 9283, decernmotinib, filgotinib, gandotinib, INCB 39110, PF 4965842, R348, AZD 1480, BMS 911543, cerdulatinib, INCB 052793, NS 018, C 410, CT 1578, JTE 052, PF 6263276, R 548, TG 02, *Lumbricus* rebellus extract, ARN 4079, AR 13154, UR 67767, CS510, VR588, DNX 04042, hyperforin, and pharmaceutically acceptable salts and combinations thereof. Such compositions may include about 0.5% (w/w) to about 10% (w/w) JAK/STAT inhibitor based on the total composition.

In some embodiments, the composition may include a base, and in particular embodiments, the base may be a liposomal base. The base in such embodiments may make up about 65% (w/w) to about 90% (w/w) of the total composition. In some embodiments, the compositions may further include a secondary active agent such as, for example, minoxidil, bimatoprost, latanoprost, finasteride, spironolactone, aldactone, kenalog-10, kenalog-40, aristospan, triamcinolone, azulfidine, sulfasalazine, sulfazine, and combinations thereof. The secondary active agent may make up about 0.25% (w/w) to about 15% (w/w) of the total composition.

Still other embodiments are directed to compositions containing about 0.5% (w/w) to about 10% (w/w) JAK/STAT inhibitor JAK/STAT inhibitor, about 1% (w/w) to about 20% (w/w) penetration enhancer, and a base. In some embodiments, the base may be a liposomal base. In various embodiments, the one or more penetration enhancer may include carriers and vehicles, chemical penetration enhancers, diols, polyols, fatty acids, fatty alcohols, fatty acid esters, surfactants, pyrrolidones, and combinations thereof. In some embodiments, the penetration enhancer may be a chemical penetration enhancer such as, for example, dimethyl sulphoxide (DMSO), decylmethyl sulfoxide, azone (1-dodecylazacycloheptan-2-one or laurocapran), pyrrolidones, oxazolidinones, urea, and combinations thereof. In some embodiments, the JAK/STAT inhibitor may be, for example, ruxolitinib (INCB 018424), tofacitinib (CP690550), AG490, momelotinib (CYT387), partcitinib (SB 1518), baricitinib (LY3009104), fedratinib (TG101348), BMS-911543, lestaurtinib (CEP-701), fludarabine, epigallocatechin-3-gallate (EGCG), baricitinib, momelotinib, pacritinib, peficitinib, ABT 494, AT 9283, decernmotinib, filgotinib, gandotinib, INCB 39110, PF 4965842, R348, AZD 1480, BMS 911543, cerdulatinib, INCB 052793, NS 018, C 410, CT 1578, JTE 052, PF 6263276, R 548, TG 02, *lumbricus rebellus* extract, ARN 4079, AR 13154, UR 67767, CS510, VR588, DNX 04042, hyperforin, and pharmaceutically acceptable salts and combinations thereof. Such compositions may include about 0.5% (w/w) to about 10% (w/w) JAK/STAT inhibitor based on the total composition. The base in such embodiments may make up about 65% (w/w) to about 90% (w/w) of the total composition.

In some embodiments, the compositions may further include a secondary active agent such as, for example, minoxidil, bimatoprost, latanoprost, finasteride, spironolactone, aldactone, kenalog-10, kenalog-40, aristospan, triamcinolone, azulfidine, sulfasalazine, sulfazine, and combinations thereof. The secondary active agent may make up about 0.25% (w/w) to about 15% (w/w) of the total composition.

DESCRIPTION OF THE DRAWINGS

Not applicable

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 µm to 8 µm is stated, 2 µm, 3 µm, 4 µm, 5 µm, 6 µm, and 7 µm are also intended to be explicitly disclosed, as well as the range of values greater than or equal to 1 µm and the range of values less than or equal to 8 µm.

All percentages, parts and ratios are based upon the total weight of the topical compositions and all measurements made are at about 25° C., unless otherwise specified.

The singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

The word "about" when immediately preceding a numerical value means a range of plus or minus 10% of that value, e.g. "about 50" means 45 to 55, "about 25,000" means 22,500 to 27,500, etc., unless the context of the disclosure indicates otherwise, or is inconsistent with such an interpretation. For example, in a list of numerical values such as "about 49, about 50, about 55," "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The terms "administer," "administering" or "administration" as used herein refer to either directly administering a compound (also referred to as an agent of interest) or pharmaceutically acceptable salt of the compound (agent of interest) or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical, cosmetic or other agent across a tissue layer such as the stratum corneum or stratum *spinosum*.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject or enhance the texture, appearance, color, sensation, or hydration of the intended tissue treatment area. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" or "cosmetically acceptable" is employed herein to refer to those agents of interest/compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, pharmaceutically acceptable means approved by a regulatory agency of the federal or a state government or listed in the U.S. Pharmacopeia or other generally recognized pharmacopeia for use in mammals (e.g. animals), and more particularly, in humans.

The term "appreciable" is employed herein to refer to those agents of interest/compounds, salts, compositions, dosage forms, etc., which—within the scope of sound medical judgement—resulted in increased hair growth. An improvement in hair growth may be quantified by a SALT score or by a % regrowth measurement. A positive appreciable change in hair growth may not rise to a pharmaceutically acceptable or cosmetically acceptable determination.

The term "salts" as used herein embraces pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Non-limiting examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid.

The term "patient" and "subject" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

The term "treating" is used herein, for instance, in reference to methods of treating a skin disorder or a systemic condition, and generally includes the administration of a compound or composition which reduces the frequency of, or delays the onset of, symptoms of a medical condition or enhance the texture, appearance, color, sensation, or hydration of the intended tissue treatment area of the tissue surface in a subject relative to a subject not receiving the compound or composition. This can include reversing, reducing, or arresting the symptoms, clinical signs, and underlying pathology of a condition in a manner to improve or stabilize a subject's condition.

The term "SALT" refers to the Severity of Alopecia Tool, which is a statistical measurement that may be used by those skilled in the art to quantize change in the severity of alopecia in a patient or a sample of patients overall. A negative change in SALT score indicates an improvement in a subject's condition.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, analogs, compounds, ligands, structures, or groups thereof, or any members of a claimed group, less than the full measure of this disclosure can be claimed for any reason. Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Various embodiments are directed to topical compositions containing one or more Jak/STAT inhibitors for treating hair growth disorders. Other embodiments are directed to methods for treating hair growth disorders that include administering a topical composition containing one or more Jak/STAT inhibitors to a subject, and in some embodiments, the methods may include the step of administering a topical composition containing one or more JAK/STAT inhibitor to a pediatric patient. Some embodiments are directed to topical compositions containing one or more Jak/STAT inhibitors for treating nail brittleness, fragility, and pitting disorders. Other embodiments are directed to methods for treating nail brittleness, fragility, and pitting disorders that include administering a topical composition containing one or more Jak/STAT inhibitors to a subject, and in some embodiments, the methods may include the step of administering a topical composition containing one or more JAK/STAT inhibitor to a pediatric patient. The compositions of such embodiments stimulate hair growth or treat nail brittleness, fragility, and pitting without side effects associated with Jak/STAT inhibitors.

The JAK/STAT inhibitors of such embodiments encompass all Jak/STAT inhibitors known in the art including any compound that inhibits expression or activity of Jakl, Jak2, Jak3, Tyk2, STATI, STAT2, STAT3, STAT4, STAT5a, STAT5b, STAT6, OSM, gpl30, LIFR, OSM-Rp, protein or polypeptide. Such Jak/STAT inhibitors can be a protein, such as an antibody (monoclonal, polyclonal, humanized, chimeric, or fully human), or a binding fragment thereof. Antibody fragments can include, for example, single chain Fv (scFv), diabodies, Fv, and (Fab') 2, triabodies, Fc, Fab, CDRI, CDR2, CDR3, combinations of CDR's, variable regions, tetrabodies, bifunctional hybrid antibodies, framework regions, constant regions, and the like and combinations thereof. Antibodies can be obtained commercially, custom generated, or synthesized against an antigen of interest according to methods established in the art. The Jak/STAT inhibitors of such embodiments include commercially available Jak/STAT inhibitors including, for example, ruxolitinib (INCB 018424), tofacitinib (CP690550), AG490, momelotinib (CYT387), partcitinib (SB 1518), baricitinib (LY3009104), fedratinib (TG101348), BMS-911543, lestaurtinib (CEP-701), fludarabine, epigallocatechin-3-gallate (EGCG), baricitinib, momelotinib, pacritinib, peficitinib, ABT 494, AT 9283, decernmotinib, filgotinib, gandotinib, INCB 39110, PF 4965842, R348, AZD 1480, BMS 911543, cerdulatinib, INCB 052793, NS 018, C 410, CT 1578, JTE 052, PF 6263276, R 548, TG 02, *Lumbricus rebellus* extract, ARN 4079, AR 13154, UR 67767, CS510, VR588, DNX 04042, hyperforin, and the like and combinations thereof.

In some embodiments, the Jak/STAT inhibitor may be a small molecule that binds to a protein and disrupts its function. Small molecules are a diverse group of synthetic and natural substances generally having low molecular weights. They can be isolated from natural sources (for example, plants, fungi, microbes and the like), are obtained commercially and/or available as libraries or collections. Candidate small molecules that modulate a protein can be identified via in silico screening or high-through-put (HTP) screening of combinatorial libraries. Most conventional pharmaceuticals, such as aspirin, penicillin, and many chemotherapeutics, are small molecules, can be obtained commercially, can be chemically synthesized, or can be obtained from random or combinatorial libraries. In some embodiments, the agent is a small molecule that binds, interacts, or associates with a target protein or RNA. Such a small molecule can be an organic molecule that, when the target is an intracellular target, is capable of penetrating the lipid bilayer of a cell to interact with the target. Small molecules include, but are not limited to, toxins, chelating agents, metals, and metalloid compounds. Small molecules can be attached or conjugated to a targeting agent so as to specifically guide the small molecule to a particular cell.

The concentration of Jak/STAT inhibitor in such embodiments contain up to about 15% (w/w) JAK/STAT inhibitors. For example, in some embodiments, the composition may include about 0.25% (w/w) to about 15% (w/w), about 0.5% (w/w) to about 10% (w/w), about 0.75% (w/w) to about 7.5% (w/w), about 1% (w/w) to about 5% (w/w), about 1% (w/w) to about 3% (w/w), or any range or individual concentration of Jak/STAT inhibitor encompassed by these example ranges. In particular embodiments, the composition may include about 0.25% (w/w) to about 5% (w/w) ruxolitinib, tofacitinib, momelotinib, partcitinib, baricitinib, fedratinib, lestaurtinib, fludarabine, epigallocatechin-3-gallate (EGCG), momelotinib, pacritinib, peficitinib, decernmotinib, filgotinib, gandotinib, cerdulatinib, or combinations thereof, and in some embodiments, the compositions may include about 0.25% (w/w) to about 5% (w/w) ruxolitinib or a derivative, including deuterated derivatives, thereof.

In some embodiments, the compositions may contain a secondary active agent such as, for example, minoxidil, bimatoprost, latanoprost, finasteride, spironolactone, aldactone, kenalog-10, kenalog-40, aristospan, triamcinolone, azulfidine, sulfasalazine, sulfazine, and the like and combinations thereof. Such secondary active agents can be provided in any amount capable of providing treatment. For example, the compositions of embodiments may include up to about 15% (w/w), about 0.25% (w/w) to about 15% (w/w), about 0.5% (w/w) to about 10% (w/w), about 0.75% (w/w) to about 7.5% (w/w), about 1% (w/w) to about 5% (w/w), about 1% (w/w) to about 3% (w/w), or any range or individual concentration of secondary active agent encompassed by these example ranges.

The compositions of various embodiments can be in any form, and embodiments include Jak/STAT containing creams, lotions, foams, liniments, balms, ointments, soaps, shampoos, and the like.

Creams refer to semi-solid emulsions of oil and water in approximately equal proportions. They are divided into two types: oil-in-water (O/W) creams, composed of small droplets of oil dispersed in a continuous phase; and water-in-oil (W/O) creams, composed of small droplets of water dispersed in a continuous oily phase. Creams can provide a barrier to protect the skin. This may be a physical barrier or a chemical barrier as with UV-absorbing compounds. To aid in the retention of moisture (especially water-in-oil creams), creams are usually used for a variety of purposes including cleansing, emollient effects, and as a vehicle for drug substances such as local anesthetics, anti-inflammatoires (NSAIDs or corticosteroids), hormones, antibiotics, antifungals or counter-irritants.

Lotions are low-to medium-viscosity topical preparation. Most lotions are oil-in-water emulsions containing an emulsifier such as cetyl alcohol to prevent separation of these two phases. Lotions can include fragrances, glycerol, petroleum jelly, dyes, preservatives, proteins and stabilizing agents.

Pharmaceutical foams are pressurized dosage forms containing one or more active ingredients that, upon valve actuation, emit a fine dispersion of liquid and/or solid materials in a gaseous medium. Foam formulations are generally easier to apply, are less dense, and spread more easily than other topical dosage forms. Foams may be formulated in various ways to provide emollient or drying functions to the skin, depending on the formulation constituents. Accordingly, this delivery technology is a useful addition to the spectrum of formulations available for topical use.

Liniments or balms are topical formulations that are of a similar viscosity to lotions and less viscous than an ointment or cream. Liniments are generally applied with friction by rubbing the liniment into the skin. Liniments typically are formulated from alcohol, acetone, or similar quickly evaporating solvents and may contain counterirritant aromatic chemical compounds such as methyl salicilate, benzoin resin, or capsaicin.

Ointments are compositions in which oil and water are provided in a ratio of from 7:1 to 2:1, from 5:1 to 3:1, or 4:1. Ointments are generally formulated using oils, waxes, water, alcohols, petroleum products, water, and other agents to prepare formulations with various viscosities and solvent properties. Commonly used formulations include oleaginous base (White Ointment), absorption base, W/O emulsion base (Cold Cream type base), O/W emulsion base (Hydrophilic Ointment), water soluble base, in addition to others. These preparations are used to dissolve or suspend substances or products with medicinal or cosmetic value.

In some embodiments, the formulations can be in the form of a soap, which are formulations that comprise a salt of a fatty acid. Soaps are mainly used as surfactants for washing, bathing, and cleaning, but they are also used in textile spinning and are important components of lubricants. Soaps for cleansing are usually obtained by treating vegetable or animal oils and fats with a strongly alkaline solution. Fats and oils are composed of triglycerides; three molecules of fatty acids are attached to a single molecule of glycerol. The alkaline solution, which is often called lye (although the term "lye soap" refers almost exclusively to soaps made with sodium hydroxide), is believed to promote a chemical reaction known as saponification. In saponification, the fats are first hydrolyzed into free fatty acids, which then combine with the alkali to form crude soap. Glycerol (glycerine) is usually liberated and is either left in or washed out and recovered as a useful byproduct, depending on the process employed.

In some embodiments, the topical formulations can be in the form of a shampoo, which is a hair care product used for the removal of oils, dirt, skin particles, dandruff, environmental pollutants, and other contaminant particles that gradually build up in hair. A goal may be to remove the unwanted build-up without stripping out so much sebum as to make hair unmanageable.

Example compositions may include various known components. For example, in some embodiments, the composition may include a solvent such as isopropyl alcohol, dipropylene glycol methyl-ether, butylated hydroxytoluene dipropylene glycol monomethyl-ether, 1-methoxy 2-propanol (glysolv PM/lcinol PM), Ethylene glycol monobutyle-ther (butyl glyxolv/butyl icinol), Butyl di glysolv (butyl-icinol), Transcutol, propylene glycol (PG), N-methyl-2 pyrrolidone (NMP), methylene chloride, diethyl ether, ethanol, acetonitrile, ethyl acetate, benzyl alcohol, a combination of natural oil; ethylene glycol, propylene glycol, dimethyl polysiloxane (DMPX), oleic acid, caprylic acid, 1-octanol, ethanol (denatured or anhydrous), liposomal compositions, suitable plant oils, such as Aloe vera derivatives or sesame seed oil or derivatives thereof, acrylic polymers, rubber-based polymers, polysiloxane-based polymers, polyvinylpyrrolidone-based polymers, dimethylsulfoxide (DMSO), dimethylformamide (DMF), dimethylacetamide, N-methyl-2-pyrrolidone, hexamethylphosphoramide (HMPA), lecithin, Transfersomes® (bi-component vesicular aggregates), ethosomes, azone, castor oil derivatives, such as ethoxylated castor oil, jojoba oil derivatives, corn oil derivatives, emu oil derivatives, and the like and combinations thereof. The solvent can be present in a concentration of about 5.0% (w/w) to about 15.0% (w/w)., about 6.0% (w/w) to about 10.0% (w/w), about 7.5% (w/w) to about 10.5% (w/w), about 8.0% (w/w) to about 10.0% (w/w), or any range or individual concentration of solvent encompassed by these example ranges.

In certain embodiments, the compositions may include a base such as, for example, white petrolatum, white petrolatum USP, mineral jelly, petroleum jelly, yellow petrolatum, yellow soft paraffin, white soft paraffin, fats, waxes, sterols, fat-soluble vitamins, monoglycerides, diglycerides, triglycerides, phospholipids, and the like and combinations thereof. In some embodiments, the base may be a liposomal base. Liposomal bases are an emulsion that includes a lipophilic component and an aqueous component that can be in the form of a lotion, a cream, a gel, or a paste. Examples of suitable liposomal bases include PCCA Lipoderm®, Lipoderm ActiveMax™, Anhydrous Lipoderm, and Lipoderm High Molecular Weight™ PCCA. Such liposomal base formulations can include, for example, about 60-80% wt/wt water combined with glycerin, C12-15 alkyl benzoate, glyceryl stearate, dimethicone, cetearyl alcohol, cetearyl glucoside, polyacrylamide, cetyl alcohol, magnesium aluminum silicate, xanthan gum, aloe vera (aloe barbadensis), tocopheryl acetate (vitamin E acetate), *Prunus amygadalus amara* (bitter almond) kernel oil, *Vitis vinifera* (Grape) seed extract, *Triticum vulgare* (wheat) germ oil, retinyl palmitate (vitamin A palmitate), ascorbyl palmitate (vitamin C palmitate), Pro-Lipo Multi-emulsion Liposomic System, tetrasodium EDTA, phenoxyethanol, sodium hydroxymethylglycinate and the like and combinations thereof.

The amount of base in the compositions of embodiments can vary and will depend on the amounts of the other components. More base can be added to compensate for smaller amounts of other components in the desired topical pharmaceutical formulation. In some embodiments, the base may be present in a concentration of about 65% (w/w) to about 90% (w/w) of the total composition, or any range or individual concentration known in the art.

In some embodiments, the compositions may include an antioxidant. Such antioxidant may be, for example, butylated hydroxytoluene, ascorbic acid, ascorbic palmitate, butylated hydroxyanisole, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone, tocopherol, and the like and pharmaceutically acceptable salt or ester thereof or combinations thereof. The antioxidant can be presention in a concentration of about 0.01% (w/w) to about 1% (w/w) of the total composition or any individual concentration encompassed by this example range.

In some embodiments, the composition may include an emulsifying agent including, for example, various monoglycerides, diglycerides, triglycerides, and blends thereof at a concentration of about 3% (w/w) to about 10% (w/w) of the total composition.

In some embodiments, the compositions may further include an anti-acne compound such as, for example, salicylic acid and benzoyl peroxide. The amount of the anti-acne compound in the topical formulation is not particularly limited, so long as it is a therapeutically effective amount, typically, about 0.01% (w/w) to 5% (w/w) of the total composition.

In some embodiments, the compositions may further include a humectant that provides soothing, smoothing, moisturizing, or protects the skin. The humectant is not limited and can be, for example, calamine, dodecylsulphate, sodium lauryl sulphate (SLS), a polyoxyethylene ester of polysorbitan, such as monooleate, monolaurate, monopalmitate, monostearate esters, esters of sorbitan, the polyoxyethylenes ethers, the sodium dioctylsulphosuccinate (DOSS), lecithin, and sodium docusate. The amount of humectant in such compositions may be about 0.01% (w/w) to 5% (w/w) of the total composition.

In some embodiments, the composition may further include a UV-absorbing compound such as, for example, glyceryl PABA, padimate O, roxadimate, dioxybenzone, oxybenzone, sulisonbenzone, octocrylene, octyl methoxycinnamate, ethoxyethyl p-methoxycinnamate, homomenthyl salicylate, ethylhexyl salicylate, trolamine salicylate, avobenzone, ecamsule, ensulizole, bemotrizinol, bisoctrizole, and the like and combinations thereof. The amount of UV-absorbing compound may be about 0.01% (w/w) to 5% (w/w) of the total composition.

In some embodiments, the composition may further include an analgesic agent such as, for example, methyl salicylate, codeine, morphine, methadone, pethidine, buprenorphine, hydromorphine, levorphanol, oxycodone, fentanyl, a non-steroidal anti-inflammatory drug (NSAID), and the like and cobinations thereof. The amount of the analgesic agent such compositions may be about 0.01% (w/w) to 5% (w/w) of the total composition.

Particular compositions encompassed by the various embodiments described above include 0.6% to 2% tofacitinib, liposomal cream base, DMSO, and propylene glycol; 06% to 2% tofacitinib citrate, DMSO, and ethyl alcohol; 0.6% to 2% ruxolitinib, liposomal cream base, and DMSO, and 0.6% to 2% ruxolitinib, DMSO, ethyl alcohol, and propylene glycol. In certain embodiments, the Jak/STAT inhibitor may be a salt form of tofaciticib or ruxolitinib such as tofaciticib citrate, tofaciticib phosphate, tofaciticib hydrochloride, ruxolitinib citrate, ruxolitinib phosphate, or ruxolitinib hydrochloride.

The compositions of the various embodiments described herein may include one or more penetration enhancers. The penetration enhancer in the compositions of various embodiments described above may be present in an amount about 0.5% (w/w) to about 40% (w/w), about 1% (w/w) to about 20% (w/w), about 5% (w/w) to about 15% (w/w) based on the total composition or any range or individual concentration encompassed by these example ranges.

Penetration enhancers can have various forms. For example, in some embodiments, the penetration may be a carrier and vehicle such as microcapsules or nanocapsules, nanoemulsions, submicron emulsions, miniemulsions, solid lipid nanoparticles, multiple emulsions, microemulsions, liposomes, niosomes, transfersomes (i.e. vesicles composed of phospholipids and 10% to 25% surfactant such as sodium cholate and 3% to 10% ethanol), ethosomes, aquasomes, and the like and combinations thereof. In other embodiments, the penetration enhancer may be a chemical penetration enhancer such as a sulphoxide, for example, dimethyl sulphoxide (DMSO), decylmethyl sulfoxide, azone (1-dodecy-lazacycloheptan-2-one or laurocapran), pyrrolidones such as N-methyl pyrrolidone, 2-pyrrolidone and N-cyclohexyl-2-pyrrolidone, and mixtures thereof, oxazolidinones, and urea. In further embodiments, the penetration enhancers may be diols such as 1,2-hexanediol, butylene glycol, diethylene glycol, dipropylene glycol, ethyl hexanediol, ethylene glycol, hexylene glycol, pentylene glycol, propylene glycol, propylene glycol monolaurate, tetraethylene glycol, triethylene glycol, tripropylene glycol, polyethylene glycol and polypropylene glycol, and mixtures thereof or polyols such as butanetriol, glycerol and 1,2,6-hexanetriol, and mixtures thereof. In still other embodiments, the penetration enhancers may be fatty acids such as essential oil, terpenes, terpenoids, oleic acid, capric acid, hexanoic acid, lauric acid, linoleic acid, linolenic acid, propionic acid and vaccenic acid, and mixtures thereof. In some embodiments, the penetration enhancers may be a fatty alcohol such as cetyl alcohol, stearyl alcohol, decanol, tridecanol, lauryl alcohol, linolenyl alcohol and oleyl alcohol, and mixtures thereof or a fatty acid ester such as glycerol monolaurate, glycerol monooleate, glycerol monolinoleate, isopropyl isostearate, isopropyl palmitate, isopropyl myristate, diethylsebacate, sorbitan monopalmitate, sorbitan oleate, sorbitan dilaurate, sorbitan trioleate, propylene glycol monolaurate and sucrose monolaurate, and mixtures thereof. In further embodiments, the penetration enhancer may be a surfactant. In still further embodiments the penetration enhancer may be a combination of one or more classes of penetration enhancer.

Other embodiments of the invention include methods for treating hair growth disorders or hair loss by administering the compositions described above. Such methods are not limited to particular indications; however, the compositions described herein can be particularly useful for treating alopecia areata, alopecia totalis, alopecia universalis, vitiligo, and graft versus host disease. Other indications that can be treated by administering the compositions of various embodiments, include telogen effluvium, tinea capitis (dermatophytosis), hypotrichosis, hereditary hypotrichosis simplex, frontal fibrosing alopecia, cicatricial alopecia, lichen planopilaris, ring alopecia, chemotherapy induced alopecia, and the like.

The methods of various embodiments may include the steps of administering a composition of the various embodiments described above to the skin of subject in need of treatment. In some embodiments, the step of administering can be carried out one, two, three, four, or more times per day, and administering can be carried out the prescribed number of times per day for one week to six months. Embodiments are not limited to subjects of a particular patient population; however, in certain embodiments, the method may be used on pediatric patients, aged 1 to 18 years, aged 1 year to 15 years, aged 1 year to 10 years, or any age or age range encompassed by these example ages. Without wishing to be bound by theory, pediatric patients may respond more readily to treatment with the compositions of embodiments.

The step of administering can be carried out by various means. For example, administering can be accomplished by applying the composition to the skin of a subject, and in some embodiments, the skin may be massaged or rubber to facilitate uptake of the JAK/STAT inhibitor. In some embodiments, administering may include applying mechanical force or energy to the skin of the subject to facilitate uptake of the JAK/STAT inhibitor. For example, administering includes injecting the composition into the skin of the subject using microneedles. In other embodiments, administering may accomplished using electroporation, iontophoresis, ultrasound, laser radiation and photomechanical waves, magnetophoresis, thermophoresis, radio frequency, suction ablation, skin abrasion and the like and combinations thereof. As is known in the art, certain means for administering may require the use of particular components of the formulation. Such components are described above and can be appropriately incorporated into the compositions.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

Compositions for treating localized hair loss caused by alopecia areata containing 1% (w/w) or 2% (w/w) topical JAK inhibitor, Ruxolitinib or Tofacitinib, in a liposomal base were made. These compositions were topically administered to pediatric patients having hair loss caused by alopecia areata. Results are presented in TABLE 1.

TABLE 1

| Number | Composition | Duration | Response (% Regrowth) |
|---|---|---|---|
| 1 | Tofactinib 2% (w/w) | ~3 months | ~20% |
| 2 | Ruxolitinib 2% (w/w) then tofacinib 1% (w/w) | 3 months | 0% |
| 3 | Ruxolitinib 1% (w/w) | 18 months | ~75% |
| 4 | Tofactinib 2% (w/w) | 9 months | 95% |
| 5 | Tofactinib 2% (w/w) | ~1 year | 80% |
| 6 | Tofactinib 2% (w/w) | 3 months | 0 |

These results provide an average improvement in hair growth of about 37%, with 67% of the patients positively responding to treatment.

Example 2

Topical compositions containing a JAK inhibitor, Tofacitinib and base were made, and these compositions were administered to pediatric patients exhibiting hair loss caused by alopecia areata, alopecia totalis, and alopecia universalis. Results are provided in TABLE 2.

TABLE 2

| Number | Composition | Duration (weeks) | Response (Change in SALT score) | Cosmetic Improvement |
|--------|-------------|------------------|--------------------------------|----------------------|
| 1 | Tofactinib 2% (w/w) in liposomal base | 29 | −17 | Appreciable |
| 2 | Tofactinib 2% (w/w) in liposomal base | 12 | +10 | Not appreciable |
| 3 | Tofactinib 2% (w/w) in liposomal base | 12 | 0 | Not appreciable |
| 4 | Tofactinib 2% (w/w) in liposomal base | 72 | −89.5 | Cosmetically acceptable |
| 5 | Tofactinib 2% (w/w) in liposomal base | 40 | −5 | Appreciable |
| 6 | Tofactinib 2% (w/w) in liposomal base | 54 | −90 | Cosmetically acceptable |
| 7 | Tofactinib 2% in Verabase BID, methotrexate, triamcinolone acetonide injectable solution | 28 | −26 | Cosmetically acceptable |
| 8 | Tofactinib 2% (w/w) in liposomal base | 25 | −92 | Cosmetically acceptable |
| 9 | Tofactinib 2% (w/w) in liposomal base, mometasone, methotrexate | 24 | −24 | Appreciable |
| 10 | Tofactinib 2% (w/w) in liposomal base | 8 | 0 | Not appreciable |
| 11 | Tofactinib 2% (w/w) in liposomal base | 76 | −21.5 | Appreciable |

Average SALT change: −32

These results provide an average improvement in hair growth of about-32 SALT score. 73% of the patients positively responded to treatment and 64% of patients exhibiting appreciable or cosmetically acceptable improvement in hair growth.

Example 3

A composition for treatment of nail brittleness, fragility, and/or pitting containing 2% Tofacitinib, 20% DMSO, 8% Span 80, and 3% Emulsifix-205 was made and administered to patients exhibiting hair loss caused by alopecia areata, alopecia totalis, and alopecia universalis. The patients exhibited improved nail consistency and strength throughout the course of treatment.

The invention claimed is:

1. A method for treating nail brittleness, fragility, or pitting comprising administering a topical composition to a subject in need thereof, wherein the composition comprises a JAK/STAT inhibitor, a base, a penetration enhancer, and an emulsifying agent, and wherein the JAK/STAT inhibitor is about 2% (w/w) of the total composition;

the penetration enhancer is dimethyl sulphoxide (DMSO) and about 20% (w/w) of the total composition;

the base is about 65% (w/w) to about 75% (w/w) of the total composition and is selected from the group consisting of white petrolatum, white petrolatum USP, mineral jelly, petroleum jelly, yellow petrolatum, yellow soft paraffin, white soft paraffin, fats, waxes, sterols, fat-soluble vitamins, monoglycerides, diglycerides, triglycerides, liposomal base, and combinations thereof; and the emulsifying agent is about 8% (w/w) of the total composition.

2. The method of claim 1, wherein the subject has a disorder selected from the group consisting of alopecia areata, alopecia totalis, alopecia universalis, vitiligo, graft versus host disease, telogen effluvium, tinea capitis (dermatophytosis), hypotrichosis, hereditary hypotrichosis simplex, frontal fibrosing alopecia, cicatricial alopecia, lichen planopilaris, ring alopecia, and chemotherapy induced alopecia.

3. The method of claim 1, wherein the JAK/STAT inhibitor is selected from the group consisting of ruxolitinib, tofacitinib, fedratinib, lestaurtinib, fludarabine, epigallocatechin-3-gallate (EGCG), baricitinib, momelotinib, pacritinib, peficitinib, decernmotinib, filgotinib, gandotinib, cerdulatinib, hyperforin, and pharmaceutically acceptable salts and combinations thereof.

4. The method of claim 1, wherein the emulsifying agent is sorbitan monooleate.

5. The method of claim 1, wherein the composition is administered at least once per day.

6. The method of claim 1, wherein the JAK/STAT inhibitor is tofacitinib or a pharmaceutically acceptable salt thereof.

7. The method of claim 1, wherein the composition further comprises a solvent.

* * * * *